(12) United States Patent
    Kennedy

(10) Patent No.: US 9,856,429 B2
(45) Date of Patent: Jan. 2, 2018

(54) MANURE TREATMENT PROCESS WITH ANAEROBIC DIGESTER

(71) Applicant: QUALITY FLOW, INC., Northbrook, IL (US)

(72) Inventor: Peter Kennedy, Gurnee, IL (US)

(73) Assignee: QUALITY FLOW, INC., Northbrook, IL (US)

( * ) Notice: Subject to any disclaimer, the term of this patent is extended or adjusted under 35 U.S.C. 154(b) by 165 days.

(21) Appl. No.: 14/543,068

(22) Filed: Nov. 17, 2014

(65) Prior Publication Data

US 2015/0140630 A1    May 21, 2015

Related U.S. Application Data

(60) Provisional application No. 61/905,397, filed on Nov. 18, 2013.

(51) Int. Cl.
    *C10L 5/42* (2006.01)
    *C10L 5/08* (2006.01)
    (Continued)

(52) U.S. Cl.
    CPC ............... *C10L 5/42* (2013.01); *C10L 5/08* (2013.01); *C10L 5/361* (2013.01); *C10L 9/083* (2013.01); *C12P 5/023* (2013.01); *C10L 2200/0469* (2013.01); *C10L 2290/06* (2013.01); *C10L 2290/08* (2013.01); *C10L 2290/26* (2013.01); *C10L 2290/30* (2013.01);
    (Continued)

(58) Field of Classification Search
    CPC ...... C10L 5/42; C10L 5/08; C10L 2200/0469;
    C10L 2290/06; C10L 2296/08; C10L 2290/30; C10L 2290/54; C10L 5/361; C10L 9/083; C10L 2290/26; C10L 2290/50; C12P 5/023; Y02E 50/10; Y02E 50/15; Y02E 50/30
    See application file for complete search history.

(56) References Cited

U.S. PATENT DOCUMENTS 4,624,417 A    11/1986   Gangi
6,190,566 B1 *  2/2001   Kolber ................ A01K 1/0103
                                                         119/447
(Continued)

FOREIGN PATENT DOCUMENTS

EP         1688475       *  8/2006
WO    2012126096 A1        9/2012
WO      2013036694        3/2013

OTHER PUBLICATIONS iCAST—International Center for Appropriate and Sustainable Technology, Cow Power: A guide to harnessing the energy in livestock waste. Colorado, USA (2009).*
(Continued)

*Primary Examiner* — Cephia D Toomer
(74) *Attorney, Agent, or Firm* — Greer, Burns & Crain, Ltd.

(57) ABSTRACT

A process is provided for converting waste fibers to solid fuel. The process includes providing a supply of animal waste including the waste fibers in a predetermined quantity, subjecting the supply of animal waste to anaerobic digestion, producing a waste byproduct, dewatering the waste byproduct, and compressing the dewatered waste byproduct to form briquettes.

17 Claims, 1 Drawing Sheet

(51) Int. Cl.
    *C12P 5/02*    (2006.01)
    *C10L 5/36*    (2006.01)
    *C10L 9/08*    (2006.01)

(52) U.S. Cl.
    CPC ....... *C10L 2290/50* (2013.01); *C10L 2290/54* (2013.01); *Y02E 50/10* (2013.01); *Y02E 50/15* (2013.01); *Y02E 50/30* (2013.01)

(56) References Cited

U.S. PATENT DOCUMENTS

| | | | |
|---|---|---|---|
| 6,299,774 B1 * | 10/2001 | Ainsworth | C02F 3/28 |
| | | | 210/178 |
| 8,317,034 B2 | 11/2012 | Fetrow | |
| 8,388,813 B1 * | 3/2013 | Livingston | C10B 1/10 |
| | | | 202/117 |
| 2011/0089271 A1 | 4/2011 | Werner | |
| 2011/0219679 A1 | 9/2011 | Budarin et al. | |
| 2011/0258914 A1 | 10/2011 | Banasiak et al. | |
| 2013/0055631 A1 | 3/2013 | Camper et al. | |
| 2013/0295628 A1 | 11/2013 | Retsina et al. | |
| 2014/0069798 A1 | 3/2014 | Hayward et al. | |

OTHER PUBLICATIONS

Gooch et al, Sand for Bedding Dairy Cow Stalls, Biological and Environmental Engineering Department Cornell University (2002).*

International Search Report from International Application No. PCT/US2014/065934, dated Mar. 3, 2015.

* cited by examiner

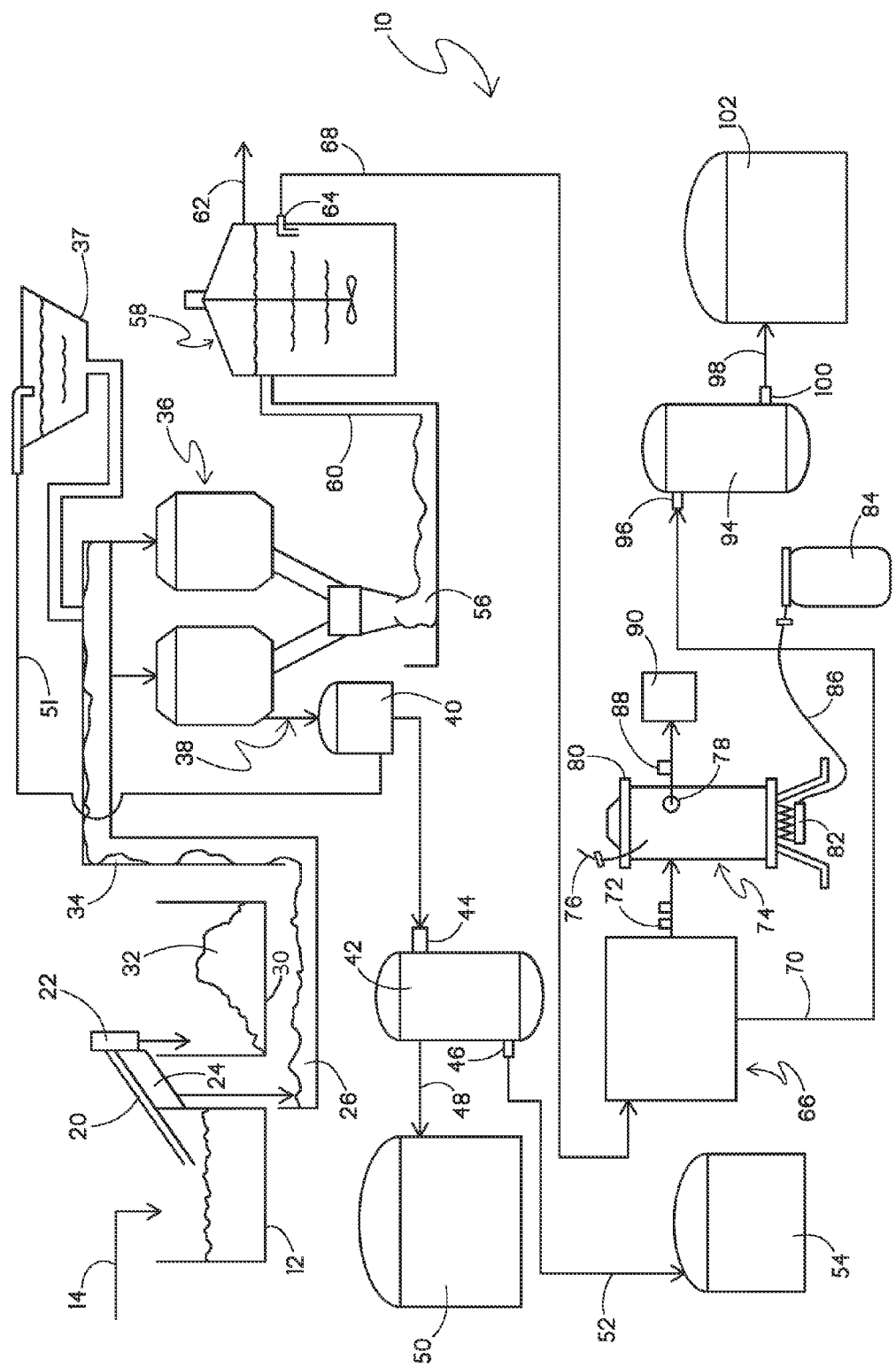

MANURE TREATMENT PROCESS WITH ANAEROBIC DIGESTER

CROSS REFERENCE

The present invention claims priority to a U.S. provisional patent application Ser. No. 61/905,397 filed on Nov. 18, 2013 under 35 U.S.C. §119(e), which is incorporated by reference.

FIELD OF THE INVENTION

The present invention is broadly concerned with processes designed to obtain fuel formed from dairy livestock waste and more particularly, a process for creating fuel from anaerobic digester waste products.

BACKGROUND

There is a tremendous amount of dairy manure waste generated by dairy farms each year that must be managed, estimated to be in the range of 694,950 tons per day generated in the US. However, there are limited options for disposing of this material, specifically manure coming from dairy Concentrated Animal Feeding Operations (CAFOs). Due to the high density of cows in such facilities, an extremely large quantity of manure is produced daily, resulting in often strong smells and continual odors that are objectionable to many people living near the facilities. Currently, the waste is usually stored in lagoons due to the relatively high percentage of water in the waste. However, lagoons and other current methods do not eliminate odor problems from dairy farming operations. Additionally, current disposal/storage methods, along with land farming, in many cases, run the risk of contaminating the air, land, and water in and around these CAFOs. Among other thing, excessive application of manure upon fields results in unwanted runoff into water supplies. Farmers often have to pay to have the excess manure hauled to landfills.

At the same time, in the global economy, increasing quantities of fossil fuels are utilized each year for electricity production, heating, steam generation, transportation and other needs. There are continual efforts by various environmentally-minded groups to encourage the decreased consumption of fossil fuels to preserve the limited quantity of the fuels, as well as to decrease the quantity of pollutants produced by burning fossil fuels. While these efforts have had some success, there is always the need for additional processes and products which utilize energy sources other than fossil fuels.

Anaerobic digestion has been used as an initiative to manage dairy manure waste and to produce a methane biogas. The methane biogas can be converted into electricity. One aspect of the use of methane for this purpose is that since the source of supply of the gas is often remote from the electricity distribution infrastructure, much of the gas is wasted. However, despite the generation of methane through anaerobic digestion, there is still a need to dispose of the solid waste resulting from anaerobic digestion.

Additionally, many dairy farms have used dried manure waste solids as bedding for dairy cows. However, when the dried manure bedding is soiled with urine or additional fecal matter, the bedding facilitates bacteria growth. The use of dried manure waste solids as dairy cow bedding leads to poor animal health, and farmers have reacted by giving the dairy cows more antibiotics to combat ailments contracted from the bedding. As a result of dried manure waste solids bedding contamination, dairy and beef food supplies are exposed to bacteria and antibiotics through the cows. Alternatively, many dairy farms have explored the use of inorganic materials, such as sand, for bedding to minimize bacterial growth and to readily drain moisture. However, sand is more costly to use, and there is a need to optimize the use of sand as bedding at a lower cost. Also, the grade of sand used previously for animal bedding has been found to be overly coarse, which irritates the animals.

At the same time, there is always a need to improve the complete water footprint of the agricultural supply chain and community. Wastewater recovered from dairy waste manure processing can be recycled for use in irrigation or on farms. To do so, however, the wastewater needs to be disinfected to cure airborne microbial issues. Alternatively, if not recycled, the wastewater also is treated before it can be discharged safely, to reduce CAFO contribution to lake and river pollution. Nitrogen and phosphorous are two nutrients present in animal waste and in excessive amounts cause an explosion of toxic algae in lakes and rivers. Activated carbon can be used as a filter for the process wastewater. However, there is a shortage of activated carbon. Thus, activated carbon can also be very costly, and there is a need for production of activated carbon from within the agricultural supply chain.

There is a need for products and processes which can utilize the dairy waste byproduct from anaerobic digestion for producing energy in a sustainable, renewable, and efficient manner, while reducing the depletion of natural resources.

SUMMARY

The above-listed needs are met by the present process, which features the use of dairy cow manure to form a fuel product. In the present process, dairy cow manure is fed into an anaerobic digestion process, producing a methane biogas and a solid/liquid waste byproduct. The solid/liquid waste byproduct is delivered to a thermal torrefaction process to further convert dairy manure waste fibers to solid fuel. This thermal torrefaction process is described in U.S. patent application Ser. No. 14/195,313 which is herein incorporated by reference. The solid fuel can additionally be converted by further thermal torrefaction into activated carbon, which can be used to filter water from the present process to be recycled for irrigation or other farm purposes. In a related embodiment, sand used for animal bedding is recycled to remove animal waste products, which are in turn passed through the above-identified torrefaction process for utilizing the waste as fuel. The sand is separated from the waste and recycled for use as dairy cow bedding.

More specifically, a process is provided for converting waste fibers to solid fuel. The process includes providing a supply of animal waste including the waste fibers in a predetermined quantity, subjecting the supply of animal waste to anaerobic digestion, producing a waste byproduct, dewatering the waste byproduct, and compressing the dewatered waste byproduct to form briquettes.

In another embodiment, a process is provided for converting waste fibers to solid fuel. The process includes providing a supply of animal waste including a supply of sand with particle size according to ASTM C-44 or ASTM C-33 standards, with a sieve size ranging from #4 to #8 and waste fiber in a predetermined quantity, separating the supply of sand from the supply of animal waste, dewatering the supply of animal waste, compressing the dewatered supply of animal waste to form a plurality of briquettes, and torrefying the briquettes in a torrefaction reactor using a heat source at a predetermined torrefying temperature for a predetermined torrefying period.

In yet another embodiment, a process for converting waste fibers to solid fuel is provided. The process includes providing a supply of animal waste including the waste fibers in a predetermined quantity, dewatering the supply of animal waste, compressing the dewatered supply of animal waste to form briquettes, torrefying the briquettes in a torrefaction reactor using a heat source at a predetermined torrefying temperature for a predetermined torrefying period to produce solid fuel, and heating the torrefied briquettes to increase absorbency.

BRIEF DESCRIPTION OF THE DRAWING

FIG. 1 is a schematic flow chart depicting the present process.

DETAILED DESCRIPTION

Referring to FIG. 1, the present dairy manure waste fiber to energy process system is generally designated 10, and is designed for converting a byproduct of anaerobic digestion to solid fuel. A reception trough or pit 12 is supplied with a slurry 14 of dairy manure and bedding sand that was flushed from at least one dairy cow's stall. The sand will preferably have a particle size according to ASTM C-44 or ASTM C-33 standards, with a sieve size within those standards ranging from #4 to #8 to measure the sand. Because the sand is used for dairy cow bedding, the preferred range of particle sizes is comfortable for the cows, because the sand conforms to their bodies when they lie down upon it, and is non-abrasive to their hooves and udders. It is contemplated that finer sand can be used depending on environmental conditions, such as wind and rain.

The flushed manure slurry 14 in the trough or pit 12 is delivered via an inclined manure auger 20 or the like having sufficient capacity for carrying the weight and amount of the manure slurry 14 to a sand separation device 22, which is a typical solids dewatering device known in many industries, such as paper making. The sand separation device 22 separates the sand from the manure slurry 14. A tank 24 underneath the inclined manure auger 20 catches the manure liquids and solids 26. Those familiar with the art should understand the operational use of these devices, as they are commercially available from various manufacturers. In a preferred embodiment, sand is separated from the manure slurry 14 prior to anaerobic digestion and the thermal torrefaction process. Sand-laden dairy manure can be processed through anaerobic digestion, however the sand will settle at the bottom of the anaerobic digester and damage the anaerobic digester equipment over time.

Before leaving the sand separation device 22, the recovered sand is rinsed with a stream of water, sifted, then discharged into a recovered sand storage area 30, and allowed to drain. The storage are 30 is contemplated to vary in size to suit the application and also to accommodate as many 72 hours of operation of the present system. Further, as needed, partitions (not shown) may be provided in the storage area 30 to separate portions of the sand to enhance drainage of batches of sand. In a preferred embodiment, the rinsed sand 32 will drain in the recovered sand storage area 30 for up to 72 hours before it is used. Preferably, the recovered sand 32 contains between 10-12% moisture content by weight, and less than 2% organic material content (dried manure solids) by weight. The sand 32 is ready to be collected and re-deposited in the parlors for the cows' bedding. In a preferred embodiment, the sand/manure separation process recovers approximately 80-98% of the sand from the manure slurry 14.

The manure liquids and solids 26 collected in the tank 24 are then delivered via piping 34 sufficient to carry the weight and amounts of the manure liquids and solids 26 to a solid/liquid separation device 36. Also supplied to the separation device 36 is manure collected from the feedlot or other sources at 37, which represents a distinct liquids/solids separator from the separator 36, such as, but not limited to a centrifuge or other mechanical separator as described below. It is contemplated that the solid/liquid separation devices 36 and 37 can separate the manure solids and liquids 26 by using gravity, such as with a settling basin or pond, or by using a mechanical separator. Mechanical solid/liquid separation devices include, but are not limited to dewatering screens, presses, and the like. Those familiar with the art should understand the operational use of these devices as they are commercially available from various manufacturers.

The liquid 38 separated from the manure is collected in a storage tank 40. The liquid stored in the storage tank 40 is then delivered to a filtration column 42 via piping sufficient to carry the weight and amounts of the separated liquid stream 38. The liquid 38 enters the filtration column 42 through inlet 44 and exits through outlet 46. In a preferred embodiment, the separated liquid stream 38 is filtered by ultra-fine filtration, reverse osmosis or similar technology. It is also contemplated that other suitable liquid filtration methods are employed at this point in the process. The filtration column 42 separates out nitrogen, phosphorous, potassium, and other nutrients present in animal waste from the separated liquid stream 38. The nutrients are delivered via piping 48 to a storage tank 50 until they can be sold or used. Those familiar with the art are aware that nitrogen, phosphorous, and potassium are three nutrients that are in many commercially available fertilizers. To enhance the separation of solids, a recirculation conduit 51 connects the storage tank 40, preferably at the bottom with the separator 37.

The filtered water 52 exiting from outlet 46 is delivered to a storage tank 54 until further processing, and can be used to irrigate fields, be put back into use on farms or otherwise discharged safely, and in some cases is potentially potable upon completion of required further treatment steps. The filtered water 52 in storage tank 50 would need to be further disinfected to cure microbial and airborne issues. It is also contemplated that a new or existing lagoon can be used as storage for the water 52 that comes from the wastewater treatment system instead of storing the water 52 in above ground tank 54. The lagoon can be covered or open, but the manure solids must not be put into the lagoon or the usefulness of the wastewater treatment system would be obviated. In a preferred embodiment, if a reverse osmosis filtration method is used on the liquid 38, the filtered water 52 would be stored in tank 54 as it would be much cleaner and would have a higher value for use with heifers or other young developing cows.

The solids 56 separated from the manure liquids and solids 26 are delivered to an anaerobic digester 58 via substrate inflow piping 60 sufficient to carry the weight and amounts of the manure solids 56. As is known in the art, the anaerobic digester 58 produces an effluent gas 62, typically methane, and an effluent substrate 64. As is well known in the art, the effluent gas 62 from anaerobic digestion can be converted into electricity. The effluent substrate 64, which is a solid/liquid byproduct of the anaerobic digestion process, contains dairy waste fibers. These fibers are the undigested elements of the cow's diet. Optionally, the effluent substrate 64, or the digestate, can be delivered to a solids separation device (not shown) to separate solids from the digestate 64. The separated digestate solids can then be used for soil amendments, dried manure bedding for cows, fertilizer, or any additional products that are known in the art.

In a preferred embodiment, the effluent substrate (the anaerobic digestion solid/liquid byproduct) 64 is delivered to a thermal torrefaction process, generally designated 66, to further convert dairy manure waste fibers in the byproduct 64 to solid fuel through piping 68 sufficient to carry the weight and amounts of the byproduct effluent substrate 64. This thermal torrefaction process 66 is described in U.S. patent application Ser. No. 14/195,313, which is incorporated by reference. Generally, this process 66 first dewaters the waste fibers and compresses the waste fibers to form briquettes. The dewatering step produces a wastewater stream 70, which contains contaminants from the manure, such as nitrogen, phosphorous, and other nutrients present in animal waste. The compressed, dewatered briquettes are then torrefied. In a preferred embodiment, the torrefaction step lasts up to 30 minutes and is carried out in the approximate range of 600 to 700 degrees Fahrenheit. The briquettes 72 formed by the torrefaction step can be used as a solid fuel product to provide the necessary energy for the process 66.

After the torrefaction reaction, the briquettes 72 can be further heated in a reactor 74 to convert the briquettes to activated carbon, increasing the absorbency. It is contemplated that the reactor 74 used for the activated carbon conversion step can be the same machinery used in the thermal torrefaction step 66, but different reactors can also be used. The reactor 74 is preferably a furnace constructed and arranged to be capable of producing activated carbon using thermal processes, in the general range of 2,000° F., and depending on how it is heated, should have a thermometer 76 for measuring the internal temperature, as well as an external temperature gauge 78. A sealed lid 80 at the opening of the reactor 74 is necessary for reducing the entry of outside oxygen into the reactor 74. It is contemplated that the seal is pressurized, but optionally may be non-pressurized.

The external heat source, generally designated 82, is configured for generating heat applied to the reactor 74 for the activated carbon conversion step, and can be from any commercially available apparatus, such as a propane gas burner 84. The reactor 74 is preferably disposed above the gas burner 84, which is supplied with fuel by a propane tank 84 by a propane tank feed line 86.

Activated carbon has a high surface area available for adsorption, and is, therefore, useful in removing contaminants from the wastewater stream. The activated carbon conversion step within the reactor 74, in a preferred embodiment, lasts up to 20 minutes depending on the amount of briquettes 72 in the reactor 74. Also in a preferred embodiment, the activated carbon conversion step within the reactor 74 is carried out in the approximate range of 600-900 degrees Fahrenheit. The briquettes undergoing the activated carbon conversion step within the reactor 74 are tested at various time intervals with iodine to measure the iodine number. The iodine number indicates the micropore volume content of the briquettes undergoing conversion by measuring adsorption of iodine by carbon from a testing solution. Once the briquettes have the iodine number of activated carbon, the activated carbon conversion step is complete. As is known to those skilled in the art, the iodine number of activated carbons used for water treatments typically ranges from 600-1100 mg/g.

Next, the reactor 74 is removed from the external heat source 82, and allowed to cool down. While the reactor 74 is cooling down, the lid 80 should remain closed to prevent the exposure of the briquettes 72 to fresh oxygen through the ambient air.

After the activated carbon 88 is removed from the reactor 74, the activated carbon 88 can be formed as pulverized activated carbon (PAC) or granular activated carbon (GAC) in an activated carbon processor 90 to provide processed activated carbon. A filtration column 94 is prepared with the processed activated carbon. The activated carbon can be sold in bulk for flue gas remediation or without activation as carbon for agricultural soil amendments. The size and operational use of the filtration column 94 should be sufficient to handle the volumetric and mass flow rates of the wastewater stream 70. In a preferred embodiment, the filtration column 94 is a packed bed filtration column. It is also contemplated that other suitable filtration column applications are employed at this point in the process.

The wastewater stream 70 is delivered to the filtration column 94, and enters the filtration column 94 at an inlet 96. In the column 94, the wastewater stream 70 passes through the column 94 as a gravity fed system, similar to a settling tank application. The filtration column 94 reduces the amounts of salts and nutrients from the animal waste, such as nitrogen, phosphorous, and potassium present in the wastewater stream 70. The filtered wastewater stream 98 exits the filtration column 94 via outlet 100. With reduced contamination, the filtered water 98 can be used for irrigation, a water supply for dairy cows, or other useful farm purposes. The filtered water 98 is delivered to a storage tank 102 until it is used. As discussed above, it is also contemplated that a new or existing lagoon can be used as storage for the water 98 that comes from the wastewater treatment system instead of storing the water 98 in above ground tank 102. The lagoon can be covered or open, but the manure solids must not be put into the lagoon or the usefulness of the wastewater treatment system would be obviated.

While particular embodiments of the present manure treatment process with anaerobic digester have been described herein, it will be appreciated by those skilled in the art that changes and modifications may be made thereto without departing from the present disclosure in its broader aspects.

The invention claimed is:

1. A process for converting waste fibers to solid fuel, comprising:
   providing a supply of animal waste including the waste fibers in a predetermined quantity;
   separating the supply of animal waste into liquids and solids;
   subjecting the solids to anaerobic digestion, producing a waste byproduct;
   after the anaerobic digestion, dewatering the waste byproduct;
   after the dewatering step, compressing the dewatered waste byproduct to form a plurality of briquettes; and
   after the compressing step, torrefying at least one of the plurality of briquettes in a torrefaction reactor configured to receive the at least one compressed fiber briquette and provide at least one solid fuel briquette using a heat source at a predetermined torrefying temperature for a predetermined torrefying period.

2. The process of claim 1, wherein the supply of animal waste contains a supply of sand with particle size according to ASTM C-44 or ASTM C-33 standards, with a sieve size ranging from #4 to #8.

3. The process of claim 2, wherein the supply of sand is separated from the animal waste before the dewatering step.

4. The process of claim 1, wherein the torrefied plurality of briquettes are heated to increase absorbency for use as an activated carbon filter for water recovered from the dewatering step.

5. A process for converting waste fibers to solid fuel, comprising:
provided a supply of animal waste including a supply of sand with particle size according to ASTM C-44 or ASTM C-33 standards, with a sieve size ranging from #4 to #8 and waste fiber in a predetermined quantity;
separating the supply of sand from the supply of animal waste;
separating the supply of animal waste into liquids and solids;
further dewatering the solids;
after the dewatering step, compressing the dewatered solids to form a plurality of briquettes; and
after the compressing step, torrefying at least one of the plurality briquettes in a torrefaction reactor configured to receive the at least one compressed fiber briquette and provide at least one solid fuel briquette using a heat source at a predetermined torrefying temperature for a predetermined torrefying period.

6. The process of claim 5, wherein the torrefied plurality of briquettes are heated to increase absorbency for use as an activated carbon filter for water recovered from the dewatering step.

7. A process for converting waste fibers to solid fuel, said process comprising:
providing a supply of animal waste including the waste fibers in a predetermined quantity;
separating the supply of animal waste into liquids and solids;
further dewatering the solids;
after the dewatering step, compressing the dewatered solids to form a plurality of briquettes;
after the compressing step, torrefying the plurality of briquettes in a torrefaction reactor using a heat source at a predetermined torrefying temperature for a predetermined torrefying period to produce solid fuel; and
heating, in a reactor configured to receive the at least one compressed fiber briquette and provide at least one solid fuel briquette, the torrefied plurality of briquettes to increase absorbency for being used as an activated carbon filter for the water recovered from the dewatering step.

8. The process of claim 7, wherein the supply of animal waste contains a supply of sand with particle size according to ASTM C-44 or ASTM C-33 standards, with a sieve size ranging from #4 to #8.

9. The process of claim 8, wherein the supply of sand is separated from the supply of animal waste before the dewatering step.

10. The process of claim 1, wherein the torrefaction reactor comprises a sealed lid.

11. The process of claim 10 further comprising:
cooling the at least one solid fuel briquette within the torrefaction reactor.

12. The process of claim 11, wherein the sealed lid is closed while the at least one solid fuel briquette is being cooled within the torrefaction reactor.

13. The process of claim 1, wherein the heat source of the torrefaction reactor comprises an external heat source.

14. The process of claim 13, wherein the external heat source comprises a propane gas burner and wherein the torrefaction reactor is disposed above the propane gas burner.

15. The process of claim 14 further comprising:
cooling the at least one solid fuel briquette within the torrefaction reactor by removing the torrefaction reactor from the propane gas burner.

16. The process of claim 15, wherein the torrefaction reactor comprises a sealed lid.

17. The process of claim 16, wherein the sealed lid is closed while the at least one solid fuel briquette is being cooled within the torrefaction reactor.

* * * * *